United States Patent
Kamarshi et al.

(10) Patent No.: US 11,412,108 B1
(45) Date of Patent: Aug. 9, 2022

(54) OBJECT RECOGNITION TECHNIQUES

(71) Applicant: Amazon Technologies, Inc., Seattle, WA (US)

(72) Inventors: Vijay Kamarshi, Cupertino, CA (US); Prasanna Venkatesh Krishnasamy, San Jose, CA (US); Amit Tikare, Pleasanton, CA (US)

(73) Assignee: Amazon Technologies, Inc., Seattle, WA (US)

( * ) Notice: Subject to any disclaimer, the term of this patent is extended or adjusted under 35 U.S.C. 154(b) by 52 days.

(21) Appl. No.: 16/883,700

(22) Filed: May 26, 2020

Related U.S. Application Data

(63) Continuation of application No. 15/425,660, filed on Feb. 6, 2017, now Pat. No. 10,671,846, which is a
(Continued)

(51) Int. Cl.
*H04N 5/222* (2006.01)
*G01B 11/02* (2006.01)
(Continued)

(52) U.S. Cl.
CPC ......... *H04N 5/2226* (2013.01); *G01B 11/026* (2013.01); *G01S 5/00* (2013.01);
(Continued)

(58) Field of Classification Search
CPC ..... G06T 7/0022; G06T 7/0024; G06T 7/004; G06T 7/0042; G06T 7/0044;
(Continued)

(56) References Cited

U.S. PATENT DOCUMENTS 5,793,900 A  8/1998 Nourbakhsh et al.
6,961,458 B2  11/2005 Dutta et al.
(Continued)

FOREIGN PATENT DOCUMENTS

WO   WO03034361        4/2003
WO   WO-2009142841 A2 * 11/2009  ........... G06T 7/0042
WO   WO2011088053 A2   7/2011

OTHER PUBLICATIONS

Owens, "Object Detection using the Kinect". (pp. 1-24) (Year: 2012).*

(Continued)

*Primary Examiner* — Manav Seth
(74) *Attorney, Agent, or Firm* — Lee & Hayes, P.C.

(57) ABSTRACT

Techniques for efficiently identifying objects of interest in an environment and, thereafter, determining the location and/or orientation of those objects. As described below, a system may analyze images captured by a camera to identify objects that may be represented by the images. These objects may be identified in the images based on their size, color, and/or other physical attributes. After identifying these potential objects, the system may define a region around each object for further inspection. Thereafter, portions of a depth map of the environment corresponding to these regions may be analyzed to determine whether any of the objects identified from the images are "objects of interest"— or objects that the system has previously been instructed to track. These objects of interest may include portable projection surfaces, a user's hand, or any other physical object. The techniques identify these objects with reference to the respective depth signatures of these objects.

20 Claims, 5 Drawing Sheets

Related U.S. Application Data continuation of application No. 13/895,025, filed on May 15, 2013, now Pat. No. 9,563,955.

(51) Int. Cl.
| | |
|---|---|
| *H04N 13/00* | (2018.01) |
| *G06T 7/246* | (2017.01) |
| *G01S 5/00* | (2006.01) |
| *G06T 7/73* | (2017.01) |
| *G06F 3/01* | (2006.01) |
| *G06T 7/20* | (2017.01) |
| *G06V 20/00* | (2022.01) |
| *G06V 20/20* | (2022.01) |
| *G06V 20/56* | (2022.01) |
| *G06V 40/10* | (2022.01) |
| *A61B 34/20* | (2016.01) |

(52) U.S. Cl.
CPC .............. *G06F 3/017* (2013.01); *G06T 7/20* (2013.01); *G06T 7/246* (2017.01); *G06T 7/73* (2017.01); *G06V 20/00* (2022.01); *G06V 20/20* (2022.01); *G06V 20/56* (2022.01); *G06V 40/10* (2022.01); *H04N 13/00* (2013.01); *A61B 2034/2065* (2016.02); *G06T 2207/10016* (2013.01); *G06T 2207/10028* (2013.01); *G06T 2207/30196* (2013.01); *G06V 2201/07* (2022.01)

(58) Field of Classification Search
CPC ... G06T 7/0051; G06T 7/0053; G06T 7/0065; G06T 7/0071; G06T 2207/10028; G06T 7/20; G06T 7/2086; G06T 7/73; G06T 2207/10016; G06T 2207/30196; G06T 7/246; H04N 5/2226; H04N 13/00; H04N 2013/0081; H04N 13/0271; A61B 2034/2065; G06K 2209/21; G06K 9/00362; G06K 9/00671; G06K 9/00791; G06K 9/00624; G01B 11/026; G06F 3/017; G01S 5/00; G06V 2201/07; G06V 20/56; G06V 20/00; G06V 40/10; G06V 20/20

See application file for complete search history.

(56) References Cited

U.S. PATENT DOCUMENTS

| | | | |
|---|---|---|---|
| 7,330,584 B2 | 2/2008 | Weiguo et al. | |
| 7,340,077 B2 | 3/2008 | Gokturk et al. | |
| 7,365,672 B2 | 4/2008 | Keller et al. | |
| 7,418,392 B1 | 8/2008 | Mozer et al. | |
| 7,512,262 B2 | 3/2009 | Criminisi et al. | |
| 7,551,770 B2 | 6/2009 | Harman | |
| 7,583,372 B2 | 9/2009 | Shylanski et al. | |
| 7,590,262 B2 * | 9/2009 | Fujimura ........... G06K 9/00369 |
| | | | 382/103 |
| 7,720,683 B1 | 5/2010 | Vermeulen et al. | |
| 7,774,204 B2 | 8/2010 | Mozer et al. | |
| 8,073,243 B2 | 12/2011 | Mareachen et al. | |
| 8,289,316 B1 | 10/2012 | Reisman et al. | |
| 8,411,149 B2 | 4/2013 | Maison et al. | |
| 8,565,485 B2 | 10/2013 | Craig et al. | |
| 8,615,108 B1 | 12/2013 | Stoppa et al. | |
| 8,619,049 B2 | 12/2013 | Harrison et al. | |
| 8,787,663 B2 * | 7/2014 | Litvak ..................... G06T 7/521 |
| | | | 382/165 |
| 8,818,097 B2 | 8/2014 | Wernersson et al. | |
| 8,830,312 B2 | 9/2014 | Hummel et al. | |
| 8,970,696 B2 | 3/2015 | Xiong | |
| 9,087,258 B2 | 7/2015 | Yu et al. | |
| 9,111,135 B2 | 8/2015 | Hummel et al. | |
| 9,158,375 B2 | 10/2015 | Maizels et al. | |
| 9,274,608 B2 | 3/2016 | Katz et al. | |
| 9,275,277 B2 * | 3/2016 | Onen ..................... G06F 3/017 |
| 9,311,550 B2 | 4/2016 | Sun et al. | |
| 9,563,955 B1 * | 2/2017 | Kamarshi ......... G06K 9/00791 |
| 10,671,846 B1 * | 6/2020 | Kamarshi ............ H04N 5/2226 |
| 2004/0012573 A1 | 1/2004 | Morrison et al. | |
| 2004/0105573 A1 | 6/2004 | Neumann et al. | |
| 2004/0140924 A1 | 7/2004 | Keller et al. | |
| 2005/0063566 A1 | 3/2005 | Beek et al. | |
| 2008/0297482 A1 | 12/2008 | Weiss | |
| 2008/0317331 A1 | 12/2008 | Winn et al. | |
| 2009/0027337 A1 | 1/2009 | Hildreth | |
| 2009/0080715 A1 | 3/2009 | van Beek et al. | |
| 2010/0199228 A1 | 8/2010 | Latta et al. | |
| 2010/0208038 A1 | 8/2010 | Kutliroff et al. | |
| 2011/0080361 A1 | 4/2011 | Miller et al. | |
| 2011/0110585 A1 | 5/2011 | Kang et al. | |
| 2011/0134114 A1 | 6/2011 | Rais et al. | |
| 2011/0158509 A1 | 6/2011 | Li et al. | |
| 2011/0211754 A1 | 9/2011 | Litvak et al. | |
| 2011/0219340 A1 | 9/2011 | Pathangay et al. | |
| 2011/0242277 A1 | 10/2011 | Do et al. | |
| 2012/0146902 A1 | 6/2012 | Adermann et al. | |
| 2012/0212509 A1 | 8/2012 | Benko et al. | |
| 2012/0223885 A1 | 9/2012 | Perez | |
| 2012/0293402 A1 | 11/2012 | Harrison et al. | |
| 2012/0327125 A1 | 12/2012 | Kutliroff et al. | |
| 2013/0044912 A1 | 2/2013 | Kulkarni et al. | |
| 2013/0051673 A1 | 2/2013 | Wernersson et al. | |
| 2013/0184592 A1 | 7/2013 | Venetianer et al. | |
| 2014/0015930 A1 | 1/2014 | Sengupta | |
| 2014/0111483 A1 | 4/2014 | Harrison et al. | |
| 2014/0122086 A1 | 5/2014 | Kapur et al. | |
| 2014/0211992 A1 | 7/2014 | Stoppa et al. | |
| 2014/0233848 A1 | 8/2014 | Han et al. | |
| 2014/0357369 A1 | 12/2014 | Callens et al. | |
| 2015/0055828 A1 | 2/2015 | Zhao et al. | |
| 2015/0071526 A1 | 3/2015 | Nguyen et al. | |

OTHER PUBLICATIONS

Tang et al., "A Textured Object Recognition Pipeline for Color and Depth Image Data". (pp. 3467-3474). (Year: 2012).*

Final Office Action dated Nov. 16, 2019 for U.S. Appl. No. 15/425,660 "Object Recognition Techniques" Kamarshi, 8 pages.

Office action for U.S. Appl. No. 13/895,025, dated Dec. 16, 2015, Kamarshi et al., "Object Tracking Techniques", 10 pages.

Office Action for U.S. Appl. No. 15/425,660, dated May 15, 2019, Kamarshi, "Object Recognition Techniques", 17 pages.

Pinhanez, "The Everywhere Displays Projector: A Device to Create Ubiquitous Graphical Interfaces", IBM Thomas Watson Research Center, Ubicomp 2001, Sep. 30-Oct. 2, 2001, 18 pages.

* cited by examiner

OBJECT RECOGNITION TECHNIQUES

RELATED APPLICATIONS

This application is a continuation of U.S. patent application Ser. No. 15/425,660, filed on Feb. 6, 2017, which is a continuation of U.S. patent application Ser. No. 13/895,025, filed on May 15, 2013, which is now U.S. Pat. No. 9,563,955, which issued on Feb. 7, 2017, both of which are incorporated herein by reference.

BACKGROUND

Augmented reality environments allow interaction among users and both real-world objects and virtual or digital objects. To achieve these augmented reality environments, a system may project content onto projection surfaces, such walls or a portable projection surface, within an environment. In addition, this system may monitor the environment for user gestures, in response to which the system may perform predefined actions. As such, such a system may monitor the environment for certain objects of interest, such as a projection surface (for projecting content thereon) or a user's hand (for the purpose of identifying a user's gesture). However, because tracking objects in this manner may be computationally expensive, the system may have difficulty tracking these objects in real-time or near-real-time, thus lessening the experience of a user employing the system.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

FIG. 3 is an illustrative diagram of the ARFN using structured light to identify objects within an environment, such as projection surfaces, a hand of a user, and the like.

DETAILED DESCRIPTION

Described herein are systems and techniques for efficiently identifying objects of interest in an environment and, thereafter, tracking the location, pose, and/or orientation of those objects. As described below, a system may analyze one or more images captured by a camera to identify one or more objects that may be represented by the images. These objects may be identified in the images based on their size, color, and/or other physical attributes. After identifying these potential objects, the system may define a region around each object for further inspection. Thereafter, portions of a depth map of the environment corresponding to these regions may be analyzed to determine whether any of the objects identified from the images are "objects of interest"—or objects that the system has previously been instructed to track. These objects of interest may include portable projection surfaces, a user's hand, or any other physical object. The techniques identify these objects with reference to the respective depth signatures of these objects.

In one example, the system identifies and tracks a portable projection surface such that a projector of the system may project content thereon. In another example, the system identifies and tracks a hand or other body part of a user so that the system may identify when the user performs a predefined gesture that, when identified by the system, causes the system to perform a predefined action (e.g., projecting content, moving content, turning off a light in the environment, etc.).

By first coarsely identifying regions of an image that may contain objects of interest and, thereafter, analyzing only portions of a depth map corresponding to these regions, the described techniques utilize fewer computational resources and are therefore able to identify and track objects in real-time or near-real-time. Because analyzing a depth map is a computationally heavy task, only a small number of objects could be tracked if the techniques searched an entire depth image each frame.

Figure 1:
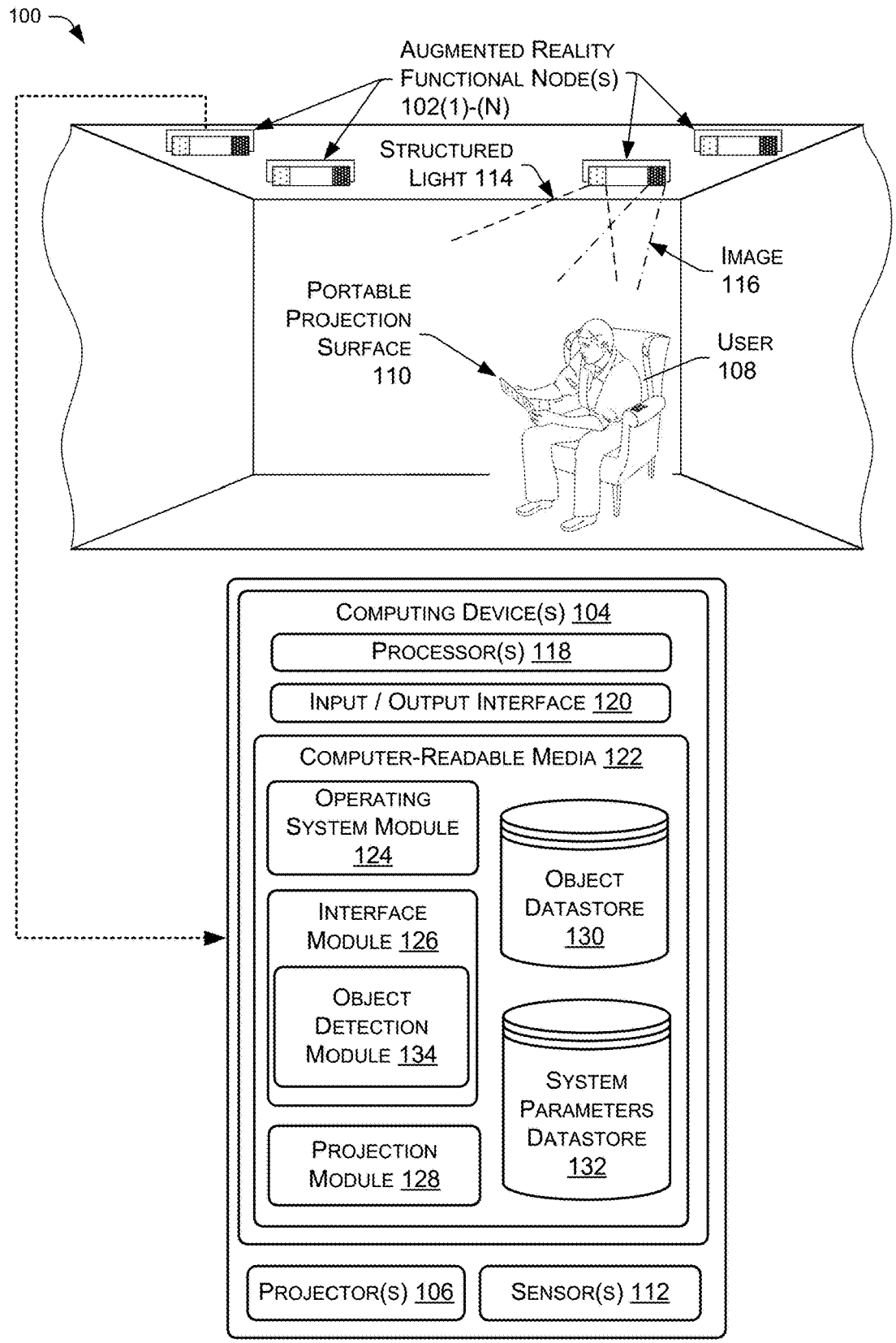
FIG. 1 illustrates an environment that includes an augmented reality functional node (ARFN) configured to track a portable projection surface and project content for a user onto the projection surface.

FIG. 1 shows an illustrative augmented reality environment 100 in which the described techniques may be performed. The environment 100 includes one or more augmented reality functional nodes (ARFNs) 102(1), . . . , 102(N) (collectively referred to as "the ARFN 102" in some instances). While the environment 100 illustrates four nodes, in some instances an environment may include any number of one or more nodes stationed in different locations throughout the environment. Furthermore, it is to be appreciated that the techniques described herein may be performed by a single ARFN, by a collection of any number of ARFNs, or by any other devices or combinations of devices having projection and imaging capabilities.

As illustrated, each ARFN 102 may include one or more computing devices 104, as well as one or more projectors 106 that, when active, project content onto any surface within the environment 100. The projected content may include electronic books, videos, images, interactive menus, or any other sort of visual content.

For instance, a user 108 within the environment 100 may request that the ARFN 102 project a particular electronic book that the user 108 wishes to read. In response, the ARFN 102 may project the book onto a projection surface within the environment 100, such as onto a portable projection surface 110. In another example, the user 108 may request that the ARFN 102 project a particular movie or show that the user 108 wishes to watch. In response, the ARFN 102 may obtain the content (locally or remotely) and may project the content onto a surface in the environment 100. In yet another example, the ARFN 102 may be configured to project a user interface (UI), such as a keyboard, a slider bar, a virtual remote control to operate a television within the environment 100, a telephone keypad, or any other type of UI. In some cases, the ARFN 102 may project the UI onto the projection surface 110, a hand of the user 108, or any other surface within the environment.

As discussed in further detail below, the ARFN 102 may include one or more sensor(s) 112 that may obtain data from the environment 100. In some implementations, the sensors 112 may include cameras (e.g., motion and/or still cameras), Time-of-Flight (ToF) sensors, audio sensors (e.g., microphones), ultrasound transducers, heat sensors, motion detectors (e.g., infrared imaging devices), depth sensing cameras, weight sensors, touch sensors, tactile output devices, olfactory sensors, temperature sensors, humidity sensors, pressure sensors, or combinations thereof. In a particular implementation, the sensors 112 may include cameras that capture images of the illustrated user 108 providing input to the ARFN 102, such as by operating a projected UI, and in response, the ARFN 102 may provide feedback to the user 108 and/or may cause performance of actions corresponding to the selection by the user 108. For instance, when the ARFN 102 projects a remote control, the ARFN 102 may provide feedback to the user 108 indicating which button(s) a user is in position to select, may identify a particular selection of the user 108 (e.g., a selection to power on the television) and, in response, may operate the television according to the identified selection. While a few examples have been given, it is to be appreciated that the ARFN 102 may project any other sort of content within the environment 100, including audio, video, or other content that can be perceived by user senses (e.g., aromatic content). In addition, the ARFN 102 may recognize and interpret gestures that are made by the user 108 without reference to a UI projected within the environment 100.

In the illustrative example of FIG. 1, one of the ARFNs 102 within the environment 100 is shown to project structured light 114. In addition, the ARFN 102 may capture one or more images 116 within the environment 100 for the purpose of identifying distortions in the structured light 114 and/or for identifying objects within the environment, as discussed in further detail below. While FIG. 1 illustrates one ARFN 102 projecting this structured light 114 and imaging the environment 100 to identify the distortions, in some implementations, one or more other ARFNs 102 may additionally or alternatively perform these functions. In either instance, by imaging the environment 100 in this manner, the ARFNs 102 may identify gestures of the user 108 within the environment 100. Such gestures may be interpreted as instructions or commands to be implemented by the ARFNs 102.

Note that certain embodiments may not involve the projection of structured light. Accordingly, it should be understood that use of structured light is but one example of various techniques that may be used in object recognition of objects in a scene. For instance, the ARFN 102 may utilize time of flight (ToF) sensors or any other type of depth-sensing techniques to aid in identifying objects with the scene.

As illustrated, the computing device 104 of the example ARFN 102 includes one or more processors 118, an input/output interface 120, and memory or computer-readable media 122. The processors 118 may be configured to execute instructions, which may be stored in the computer-readable media 122 or in other computer-readable media accessible to the processors 118.

Figure 2:
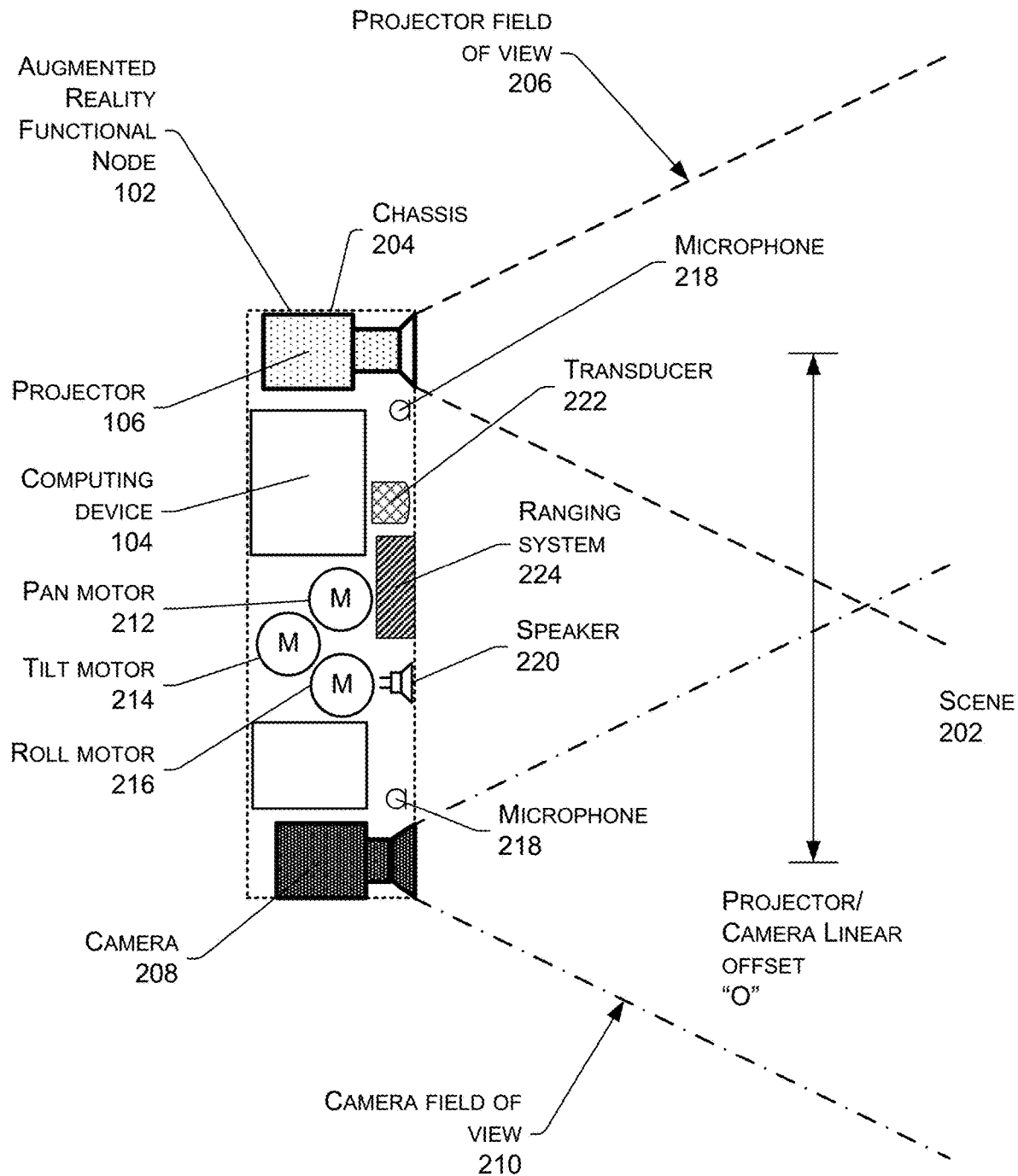
FIG. 2 illustrates an example ARFN that includes a computing device, a projector, a camera, and other selected components for allowing a user to interact with the ARFN.

The input/output interface 120, meanwhile, may be configured to couple the computing device 104 to other components of the ARFN 102, such as the projector 106, the sensors 112, other ARFNs 102, other computing devices, and so forth. The coupling between the computing device 104 and the devices may be via wire, fiber optic cable, wireless connection, or the like. Furthermore, while FIG. 1 illustrates the computing device 104 as residing within a housing of the ARFN 102, some or all of the components of the computing device 104 may reside at another location that is operatively connected to the ARFN 102. In still other instances, certain components, logic, and/or the like of the computing device 104 may reside within the projector 106, the sensors 112, or both. Therefore, it is to be appreciated that the illustration of the ARFN 102 of both FIGS. 1 and 2 is for illustrative purposes only, and that components of the ARFN 102 may be configured in any other combination and at any other location.

The computer-readable media 122, meanwhile, may include computer-readable storage media ("CRSM"). The CRSM may be any available physical media accessible by a computing device to implement the instructions stored thereon. CRSM may include, but is not limited to, random access memory ("RAM"), read-only memory ("ROM"), electrically erasable programmable read-only memory ("EEPROM"), flash memory or other memory technology, compact disk read-only memory ("CD-ROM"), digital versatile disks ("DVD") or other optical disk storage, magnetic cassettes, magnetic tape, magnetic disk storage or other magnetic storage devices, or any other medium which can be used to store the desired information and which can be accessed by the computing device 104. The computer-readable media 122 may reside within a housing of the ARFN 102, on one or more storage devices accessible on a local network, on cloud storage accessible via a wide area network, or in any other accessible location.

The computer-readable media 122 may store several modules, such as instructions, datastores, and so forth that are configured to execute on the processors 118. For instance, the computer-readable media 122 may store an operating system module 124, an interface module 126, a projection module 128, an object datastore 130, and a system parameters datastore 132.

The operating system module 124 may be configured to manage hardware and services within and coupled to the computing device 104 for the benefit of other modules. The interface module 126, meanwhile, may be configured to receive and interpret commands received from users within the environment 100. For instance, the interface module 126 may analyze and parse images captured by the sensors 112 to identify one or more hands in the environment 100. In response to recognizing a hand and identifying a gesture formed by the hand, the interface module 126 may interpret the gesture and cause the ARFN 102 to perform a corresponding action. For instance, if the user 108 within the environment 100 makes a gesture requesting that the ARFN 102 project a certain piece of content, the interface module 126 may interpret the gesture and cause the projection module 128 to project the content via the projector 106.

In addition, the interface module 126 may include an object detection module 134 that is configured to identify objects of interest within the environment. In some instances, the object datastore 130 stores an indication of "objects of interest"—or objects that the ARFN 102 has been instructed to track. In some instances, these objects include the portable projection surface 110, a hand or other body part of the user 108, or any other object. When the object detection module 134 detects an object, the module 134 may update the object datastore 130 to reflect the presence of the object within the environment 100. In addition, the module 134 may continue to track the location, pose, and/or orientation of the object and may store this information in the object datastore 130 in association with the object. Other components of the ARFN may then use this information for a variety of purposes. For instance, the projection module 128 may use this information for projecting content toward an identified projection surface (e.g., the surface 110) as the surface moves through the environment.

In order to identify one or more objects within the environment 100, the object detection module 134 may execute a first thread that performs a coarse identification of objects within the environment 100 by analyzing two-dimensional (2D) images or depth images captured by one of the sensors 112. In some instances, these images analyzed by the first thread may comprise down-sampled versions of the images captured by the image sensor. Additionally or alternatively, the algorithms used by the first thread to analyze the images may be simpler as compared to the algorithms used to more finely analyze these depth maps.

This first thread then reports this information to a coordinator thread, which compares reported locations of objects with existing information about known, tracked, objects as stored by the object datastore 130. If the coordinator thread determines that an object identified by the first thread is not currently indicated by the object datastore 130 as being within the environment 100, then the coordinator adds an indication of this new object to the object datastore 130.

After identifying a potential object of interest from the information reported by the first thread, the coordinator thread defines or "draws" a region of interest around the object of interest and launches a second thread to perform a finer level of identification. This "region of interest" comprises less than entirety of the image from which the first thread identified the object of interest. In some instances, the first thread may continue executing and examining images of the environment after the second thread begins executing. As the first thread identifies additional potential objects of interest, the first thread may launch corresponding additional "second threads" to track the additional potential objects of interest. Furthermore, if an object leaves the environment, and hence is no longer within the captured images of the environment for a threshold amount of time, then the second thread responsible for tracking this object may be terminated.

This second thread launched by the coordinator thread is a dynamic thread configured to track the object through the environment 100 in real-time or near-real-time. To do so, this second thread runs computationally heavier object recognition software to confirm that the object is indeed an object of interest and, thereafter, to track the object of interest. When doing so, however, the second thread analyzes only a portion of a depth map of the environment 100 corresponding to the region of interest defined by the coordinator thread. Because this second thread runs only in a constrained region of the depth map, this thread is able to execute in real-time or near-real-time. In addition, this second thread is able to dynamically update the object's region of interest as the object moves, keeping the execution load of the second thread small.

The second thread reports back the identity, location, pose, and/or orientation of the object of interest to coordinator thread, which in turn updates the object datastore 130. As described above, this information that the object datastore 130 stores may be used by other components in the system, such as by the projection module 128 to enable to the projector to project content toward a projection surface. Because the second thread analyzes portions of depth maps rather than the entirety of these maps, these techniques allow for tracking of multiple objects of interest in real-time or near-real-time, with only a moderate amount of execution load on the processor(s) 118.

In some instances, the first thread launches a second thread in response to identifying a potential object of interest. However, the second thread may determine that the identified potential object of interest is not in fact an actual object of interest. As such, the second thread (or the first thread) may store this indication such that the first thread does not later launch another second thread. That is, the second thread (or the first thread) may add the identified object (i.e., color, size, and other characteristics of the object) to a blacklist of objects such that the first thread no longer launches second threads in response to identifying this object.

In still other instances, the first thread may launch a second thread in response to identifying an unknown object (or identifying this unknown object more than a threshold number of times). The second thread may then track this unknown object and provide the images or other metadata to another service for identification. For instance, the second thread may provide this information to a group of one or more human users, who in turn may attempt to identify the object and make a determination as whether this object is an object of interest that should be tracked in the future. If so, then the item (i.e., its color, size, and other characteristics) may be added to the list of objects that should be tracked.

As illustrated, the computer-readable media 122 may also store the system parameters datastore 132, which is configured to maintain information about the state of the computing device 104, the projector 106, the sensors 112, and so forth. For example, and as described in detail below, the ARFN 102 may be configured to pan and tilt for the purpose of allowing the projector 106 and the sensors 112 to access different projection surfaces in the environment 100. As such, the system parameters maintained in the system parameters datastore 132 may include current pan and tilt settings of the projector 106 and the sensors 112, an indication of content that the ARFN 102 is currently projecting or otherwise outputting, and the like.

The system parameters datastore 132 (or another datastore) may further store a library of reference gestures that may be used to interpret user gestures. As illustrated, the user 108 in the environment 100 may make gestures with his body, such as hand motions, that can be captured by the sensors 112. The computing device 104 may identify motion parameters corresponding to the observed gesture and compare the observed motion parameters to those of the library of reference gestures. The computing device 104 may then classify the observed gesture based on the comparison.

FIG. 2 shows additional details of an example ARFN 102. The ARFN 102 is configured to scan at least a portion of a scene 202 and the objects therein. In a particular implementation, the scene 202 may be at least a portion of the environment 100 of FIG. 1. The ARFN 102 may also be configured to provide output, such as images, sounds, and so forth.

A chassis 204 holds the components of the ARFN 102. One or more projectors 106 may be disposed within the chassis 204 and may be configured to generate and project images into the scene 202. These images may be visible light images perceptible to the user, visible light images imperceptible to the user, images with non-visible light, or a combination thereof. The projector 106 may be implemented with any number of technologies capable of generating an image and projecting that image onto a surface, such as a display object, within the scene 202. Suitable technologies include a digital micromirror device (DMD), liquid crystal on silicon display (LCOS), liquid crystal display, 3LCD, and so forth. The projector 106 has a projector field of view 206 which describes a particular solid angle. The projector field of view 206 may vary according to changes in the configuration of the projector 106. For example, the projector field of view 206 may narrow upon application of an optical zoom to the projector 106.

One or more cameras 208 may also be disposed within the chassis 204. The camera 208 is configured to image the scene 202 in visible light wavelengths, non-visible light wavelengths, or both. The camera 208 has a camera field of view 210 that describes a particular solid angle. The camera field of view 210 may vary according to changes in the configuration of the camera 208. For example, an optical zoom of the camera 208 may narrow the camera field of view 210.

The chassis 204 may be mounted with a fixed orientation, or may be coupled via an actuator to a fixture such that the chassis 204 may move. Actuators may include piezoelectric actuators, motors, linear actuators, and other devices configured to displace or move the chassis 204 or components therein such as the projector 106 and/or the camera 208. For example, in one implementation the actuator may comprise a pan motor 212, a tilt motor 214, a roll motor 216, and so forth. The pan motor 212 is configured to rotate the chassis 204 in a yawing motion. The tilt motor 214, meanwhile, is configured to change the pitch of the chassis 204. The roll motor 216 is configured to move the chassis 204 in a rolling motion. By panning, tilting, and/or rolling the chassis 204, different views of the scene 202 may be acquired.

One or more microphones 218 may be disposed within the chassis 204, or elsewhere within the scene 202. These microphones 218 may be used to acquire input from a user in the scene 202, may be used to determine the location of a sound, or may be used to otherwise aid in the characterization of and receipt of input from the scene 202. For example, the user may make a particular noise, such as a tap on a wall or a snap of the fingers, which are pre-designated as attention command inputs. The user may alternatively use voice commands. Such audio inputs may be located within the scene 202 using time-of-arrival differences among the microphones 218 and used to summon an active zone within the scene 202.

One or more speakers 220 may also be present to provide for audible output. For example, the speakers 220 may be used to provide output from a text-to-speech module or to playback pre-recorded audio.

A transducer 222 may also reside within the ARFN 102, or elsewhere within the environment, and may be configured to detect and/or generate inaudible signals, such as infrasound or ultrasound. These inaudible signals may be used to provide for signaling between accessory devices and the ARFN 102.

The ARFN 102 may also include a ranging system 224. The ranging system 224 is configured to provide distance information from the ARFN 102 to a scanned object or a set of objects. The ranging system 224 may comprise ToF sensors, radar, light detection and ranging (LIDAR), ultrasonic ranging, stereoscopic ranging, and so forth. In some implementations the transducer 222, the microphones 218, the speaker 220, or a combination thereof may be configured to use echolocation or echo-ranging to determine distance and spatial characteristics.

In this illustration, the computing device 104 is shown within the chassis 204. However, in other implementations all or a portion of the computing device 104 may be disposed in another location and coupled to the ARFN 102. This coupling may occur via wire, fiber optic cable, wirelessly, or a combination thereof. Furthermore, additional resources external to the ARFN 102 may be accessed, such as resources in another ARFN 102 accessible via a local area network, cloud resources accessible via a wide area network connection, or a combination thereof. In still other instances, the ARFN 102 may couple to and control other devices within the environment 100, such as televisions, stereo systems, lights, and the like.

FIG. 2 also illustrates a projector/camera linear offset designated as "O". This is a linear distance between the projector 106 and the camera 208. Placement of the projector 106 and the camera 208 at a distance "O" from one another may aid in the recovery of 3D structured light data from the scene 202. The known projector/camera linear offset "O" may also be used to calculate distances, dimensioning, and otherwise aid in the characterization of objects within the scene 202. In other implementations the relative angle and size of the projector field of view 206 and camera field of view 210 may vary. Also, the angle of the projector 106 and the camera 208 relative to the chassis 204 may vary.

In other implementations, the components of the ARFN 102 may be distributed in one or more locations within the scene 202. As mentioned above, microphones 218 and speakers 220 may be distributed throughout the environment that includes the ARFN 102. The projector 106 and the camera 208 may also be located in separate chasses 204. The ARFN 102 may also include discrete portable signaling devices used by users to issue command attention inputs. For example, these may be acoustic clickers (audible or ultrasonic), electronic signaling devices such as infrared emitters, radio transmitters, and so forth.

Figure 3:
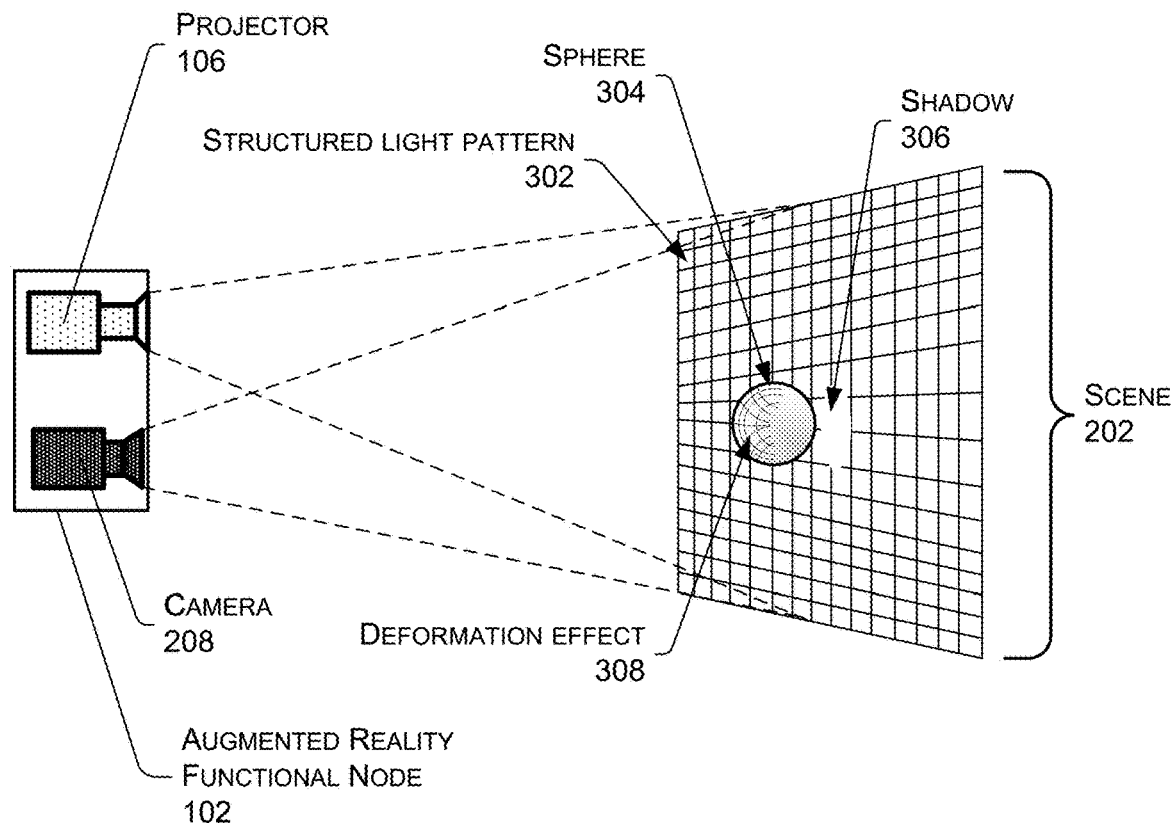

FIG. 3 is an illustrative diagram of the ARFN 102 using structured light to identify 3D information regarding users, user hands, and other objects within an environment. However, while the structured light techniques described herein provide one example for obtaining 3D information regarding these objects, it is to be appreciated that 3D information may be determined in other manners in other embodiments, such as using ToF sensors or other depth-sensing techniques.

In the instant illustration, the projector 106 projects a structured light pattern 302 onto the scene 202. In some implementations a sequence of different structured light patterns 302 may be used. This structured light pattern 302 may be in wavelengths that are visible to a user within the scene 202, non-visible to the user, or a combination thereof. The structured light pattern 302 is shown in this example as a grid for ease of illustration and not as a limitation. In other implementations other patterns, such as bars, dots, pseudorandom noise, and so forth may be used. Pseudorandom noise (PN) patterns are useful as structured light patterns because a particular point within the PN pattern may be specifically identified. A PN function is deterministic in that given a specific set of variables, a particular output is defined. This deterministic behavior allows for specific identification and placement of a point or block of pixels within the PN pattern. In some implementations, a plurality of structured light patterns 302 may be used to image the scene 202. These may include different PN patterns, geometric shapes, and so forth.

For illustrative purposes in FIG. 3, a sphere 304 is shown positioned between the projector 106 and a wall in the scene 202. A shadow 306 from the sphere 304 appears on the wall. Inspection of the sphere 304 shows a deformation or distortion effect 308 of the structured light pattern 302 as it interacts with the curved surface of the sphere 304.

In some implementations other effects, such as dispersion of the structured light pattern 302, may be used to provide information on the topology of the scene 202. Where the projector 106 and camera 208 have differing fields of view, such as shown in FIG. 2, the dispersion or change in the "density" of the structured light pattern 302 may be used to determine depth of field.

The camera 208 may detect the interaction of the structured light pattern 302 with objects within the scene 202. For example, the deformation effect 308 on the sphere 304 may be detected by the camera 208. The camera 208 may similarly identify deformation effects on users within the scene 202 and may utilize this information to identify user gestures and trajectories of these gestures. That is, the camera 208 may identify, via deformation in the structured light, a location of a selection tool (e.g., a user's finger) as this location changes over time. The ARFN 102 may then use these locations tracked over time to identify a trajectory of the gesture. The location of the selection tool may be expressed as 3D position coordinates specified relative to orthogonal X, Y, and Z axes, 3D angular orientations may be specified as rotations about the X, Y, and Z axes, or both.

Figure 4:
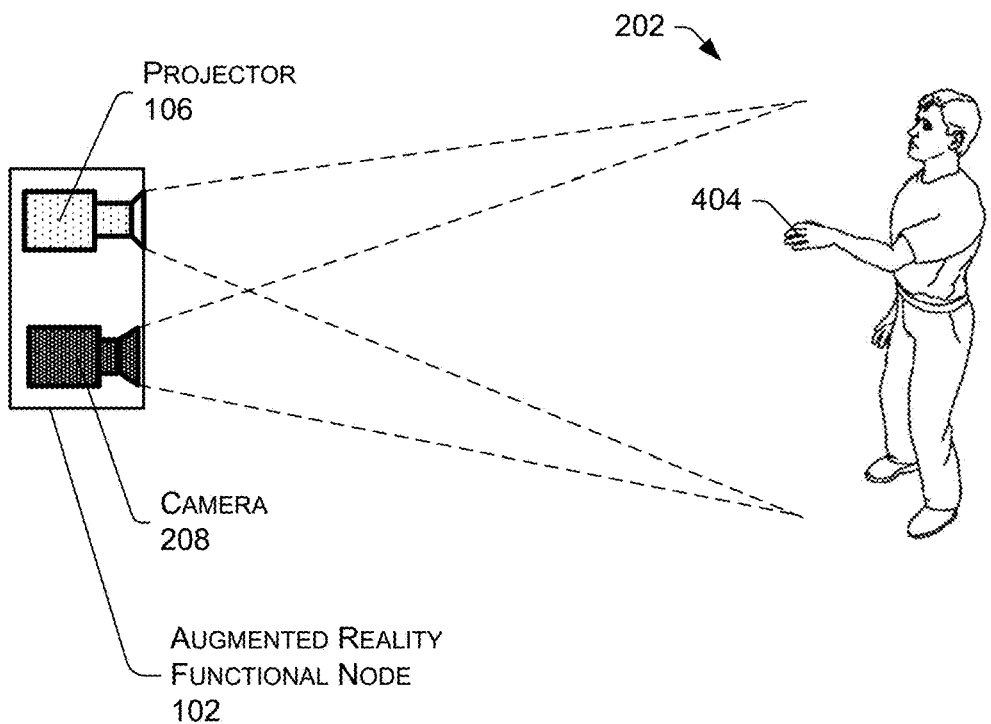
FIG. 4 is an illustrative diagram of the ARFN detecting the user's hand within an environment.

FIG. 4 illustrates an example of how the ARFN 102 may be used to observe and identify hand gestures within the scene 202. FIG. 4 shows a person 402 and the person's hand 404 as examples of objects within the environment 100 that may be analyzed by the ARFN 102.

In order to identify hand gestures, the ARFN 102 detects and tracks the hand 404 within the environment or scene 202. Specifically, the ARFN 102 may identify a sequence of hand positions or poses that form a hand gesture. A hand gesture may be defined by a series of poses of the hand 404, where each pose indicates the 3D position of the hand 404 and the 3D angular orientation of the hand 404. Position and angular orientation may be evaluated as absolute positions and orientations or as relative positions and orientations.

As an example, 3D position coordinates may be specified relative to orthogonal X, Y, and Z axes. 3D angular orientations may be specified as rotations about the X, Y, and Z axes.

As described above, the camera 208 may be used in conjunction with a structured light pattern projected by the projector 106 to capture 3D information regarding objects within the scene 202. Specifically, the projector 106 may project a structured light pattern onto the scene 202, and the camera 208 may capture a 2D image or array that indicates the resulting reflected light pattern, which is potentially distorted by objects within the scene 202. The reflected light pattern can be analyzed to reconstruct 3D characteristics or models of objects within the environment 100.

In addition to being used to observe a reflected light pattern, as described above, the camera 208 of the ARFN 102 may be used to capture 2D images of the scene 202. For example, the camera 208 may be used in conjunction with ambient lighting, with or without further illumination by the projector 106, to capture a 2D image of the environment 100. The captured 2D image may be a color or grayscale image, comprising an array of pixels defined by tone or color intensities.

As described above, the projector 106 may be configured to project non-visible light, or light of a specific wavelength that can be filtered by the camera 208 or by electronics associated with the camera 208. This may allow the ARFN 102 to obtain, from a single image capture, a 2D color image of the scene 202 and a 2D pattern image of the projected light pattern as reflected by any objects within the scene 202, such as the person 402 and/or the person's hand 404.

Note that certain embodiments may implement 3D shape detection, analysis, and reconstruction using techniques that do not involve the projection and/or analysis of structured light. Accordingly, it should be understood that structured light analysis is described as but one example of various 3D analysis techniques that may be used to identify 3D shapes within a scene or within regions of a scene.

Figure 5:
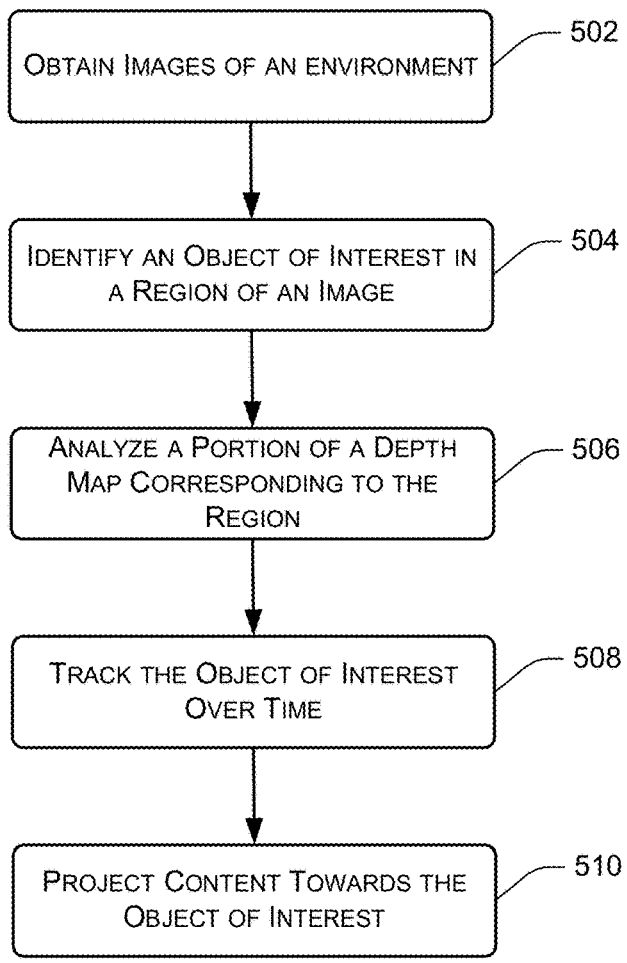
FIG. 5 illustrates an example flow diagram of a process to identify an object of interest, such as a projection surface or a user's hand, by first identifying a region of an image that may contain the object and then analyzing a portion of a depth map corresponding to the region to confirm the identification of the object.

FIG. 5 illustrates an example flow diagram of a process 500 to identify an object of interest, such as a projection surface or a user's hand, by first identifying a region of an image that may contain the object and then analyzing a portion of a depth map corresponding to the region to confirm the identification of the object.

The process 500 (as well as each process described herein) is illustrated as a logical flow graph, each operation of which represents a sequence of operations that can be implemented in hardware, software, or a combination thereof. In the context of software, the operations represent computer-executable instructions stored on one or more computer-readable media that, when executed by one or more processors, perform the recited operations. Generally, computer-executable instructions include routines, programs, objects, components, data structures, and the like that perform particular functions or implement particular abstract data types.

The computer-readable media may include non-transitory computer-readable storage media, which may include hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of storage media suitable for storing electronic instructions. In addition, in some embodiments the computer-readable media may include a transitory computer-readable signal (in compressed or uncompressed form). Examples of computer-readable signals, whether modulated using a carrier or not, include, but are not limited to, signals that a computer system hosting or running a computer program can be configured to access, including signals downloaded through the Internet or other networks. Finally, the order in which the operations are described is not intended to be construed as a limitation, and any number of the described operations can be combined in any order and/or in parallel to implement the process.

At 502, the process 500 obtains images of an environment that includes an object of interest, such as a portable projection surface, a hand of a user, or the like. At 504, the process 500 identifies, from one of the images, a region of the image that represents (i.e., includes or depicts) the object of interest. The object detection module 134, described above, may identify this region from a 2D image by image-recognition techniques, such as with reference to a shape or contour of the object, colors of the object, and/or the like.

At 506, the process 500 analyzes a portion of a depth map, with this portion corresponding to the region of the image that represents the object of interest. By analyzing only this portion, rather than the entire depth map, the process 500 utilizes fewer computational resources. In addition, analyzing the depth map may be effective to determine whether or not the object of interest is indeed present. In some instances, the object identification module 134 compares a depth signature associated with the known object of interest to depths found in the depth map to determine whether or not the object of interest is present.

After identifying the object of interest, at 508 the process 500 may track the object over time. This may include tracking its location within the environment, tracking its orientation, or the like. This information may be stored in the object datastore 130 and, thereafter, used by other components of the system. For instance, if the object of interest comprises a hand or other body part of a user, the information may be used to interpret a gesture made by the user. If, however, the object comprises a projection surface, the information may be used to determine where to project content within the environment such that the projection surface receives the content, as well as how to modify the content prior to projection to account for the orientation of the projection surface. The process 500 represents, at 510, projecting content toward the object of interest in this manner.

Figure 6:
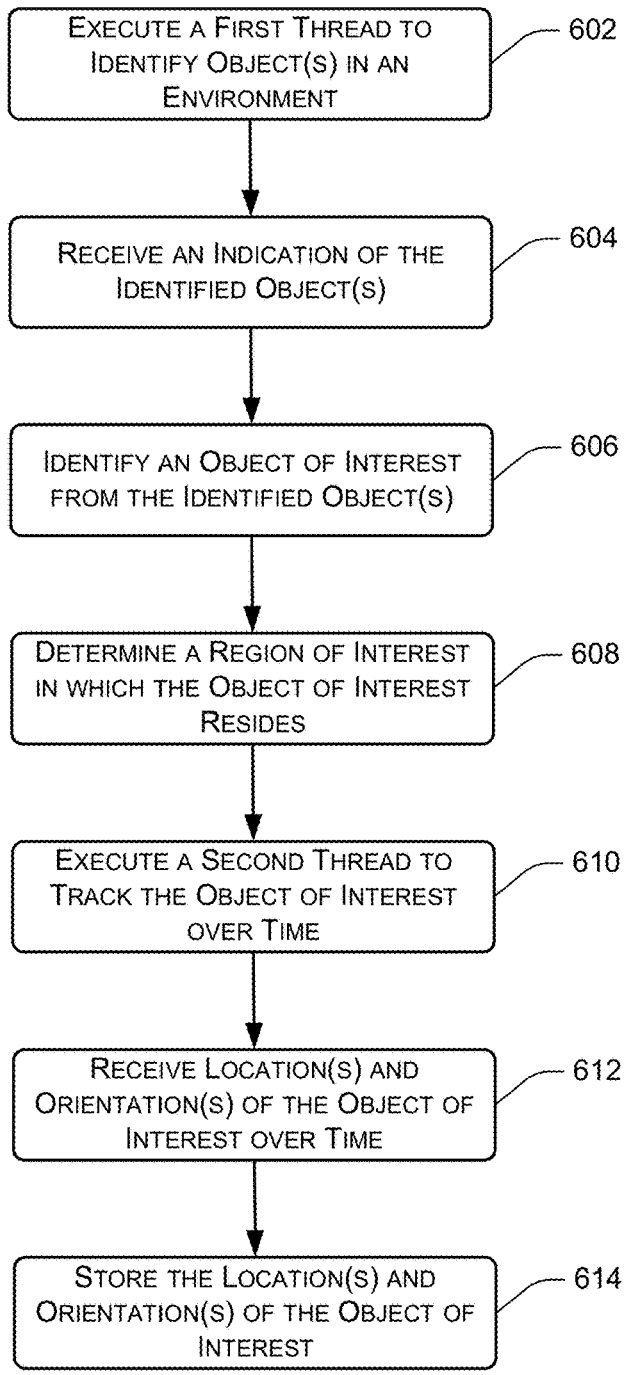
FIG. 6 illustrates an example flow diagram of a process to execute a first thread that identifies objects at a coarse level and, thereafter, executes a second thread to identify objects at a finer level.

FIG. 6 illustrates an example flow diagram of a process 600 to execute a first thread that identifies objects at a coarse level and, thereafter, executes a second thread to identify objects at a finer level.

At 602, the process 600 executes the first thread to identify, from 2D image(s), one or more objects in an environment. At 604, the process 600 receives an indication of these identified object(s). For instance, the coordinator thread described above may receive these indications and, in response, may compare the identified objects to objects indicated in the object datastore 130 to identify, at 606, one or more objects of interest in the environment. At 608, the process 600 (e.g., the first thread or the coordinator thread) may determine a region of the image that represents an object of interest. At 610, and in response, the coordinator thread may execute a second thread to confirm that the environment includes the object of interest and/or to track the object of interest over time.

At 612, the process 600 (e.g., the coordinator thread) may receive an indication of the location, pose, and/or orientation of the object as this location and/or orientation changes over time. At 614, the process 600 may store this information, such as in the object datastore 130.

Although the subject matter has been described in language specific to structural features, it is to be understood that the subject matter defined in the appended claims is not necessarily limited to the specific features described. Rather, the specific features are disclosed as illustrative forms of implementing the claims.

What is claimed is:

1. A device comprising:
   one or more processors; and
   one or more computer-readable media storing instructions that, when executed by the one or more processors, cause the device to perform operations comprising:
   generating image data using a first sensor;
   receiving an input indicating that the image data represents an object;
   generating depth map data using a second sensor; and
   based at least in part on receiving the input indicating that the image data represents the object, determining, using the depth map data, information associated with the object.

2. The device as recited in claim 1, wherein:
   the object includes a portion of a user; and
   the information includes at least one of a location of the portion of the user, a pose of the portion of the user, an orientation of the portion of the user, or a surface detail associated with the portion of the user.

3. The device as recited in claim 1, the operations further comprising:
   storing object data representing an object of interest; and
   determining that the object includes the object of interest based at least in part on the information.

4. The device as recited in claim 1, the operations further comprising identifying a gesture made by the object based at least in part on at least one of the image data or the depth map data.

5. The device as recited in claim 1, the operations further comprising:
   generating additional depth map data using the second sensor; and
   determining, based at least in part on the additional depth map data, additional information associated with the object.

6. The device as recited in claim 5, wherein:
   the information is associated with at least one of a first location, a first pose, a first orientation, or a first surface associated with the object; and
   the additional information is associated with at least one of a second location, a second pose, a second orientation, or a second surface associated with the object.

7. The device as recited in claim 1, the operations further comprising:
   storing the information associated with the object;
   after storing the information, generating additional depth map data using the second sensor, the additional depth map data representing at least a potential object of interest;
   determining, based at least in part on the additional depth map data, information associated with the potential object of interest; and
   determining that the potential object of interest includes the object based at least in part on the information associated with the object and the information associated with the potential object of interest.

8. The device as recited in claim 1, the operations further comprising:
   determining that a portion of the image data represent the object; and
   analyzing a portion of the depth map data that corresponds to the portion of the image data,
   wherein determining the information associated with the object is based at least in part on analyzing the portion of the depth map data.

9. The device as recited in claim 1, the operations further comprising outputting content based at least in part on the information.

10. A method comprising:
    storing first data representing a first object;
    generating image data using a first sensor, the image data representing a second object;
    generating depth map data using a second sensor;
    determining, based at least in part on the depth map data, information associated with the second object; and
    determining that the second object includes the first object based at least in part on the information.

11. The method as recited in claim 10, wherein:
    storing the first data representing the first object comprises storing the first data representing a portion of a user; and
    determining the information associated with the second object comprises determining, based at least in part on the depth map data, at least one of a location of the portion of the user, a pose of the portion of the user, an orientation of the portion of the user, or a surface detail associated with the portion of the user.

12. The method as recited in claim 10, further comprising identifying a gesture made by the object based at least in part on at least one of the image data or the depth map data.

13. The method as recited in claim 10, further comprising:

generating additional depth map data using the second sensor; and determining, based at least in part on the additional depth map data, additional information associated with the first object, wherein the first data represents the additional information associated with the first object.

14. The method as recited in claim 13, wherein:

determining the additional information associated with the first object comprises determining, based at least in part on the additional depth map data, at least one of a first location of the first object, a first pose of the first object, a first orientation of the first object, or a first surface detail associated with the first object; and determining the information associated with the second object comprises determining, based at least in part on the depth map data, at least one of a second location of the second object, a second pose of the second object, a second orientation of the second object, or a second surface detail associated with the second object.

15. The method as recited in claim 10, further comprising:

determining that a portion of the image data represent the object; and analyzing a portion of the depth map data that corresponds to the portion of the image data, wherein determining the information associated with the object is based at least in part on analyzing the portion of the depth map data.

16. The method as recited in claim 10, further comprising outputting content based at least in part on the information.

17. A method comprising:

generating image data using a first sensor;

generating depth map data using a second sensor;

determining information based at least in part on the depth map data;

determining that the image data represents an object; and based at least in part on determining that the image data represents the object, determining a portion of the information that is associated with the object.

18. The method as recited in claim 17, wherein:

the object includes a portion of a user; and determining the portion of the information associated with the object comprises determining at least one of a location of the portion of the user, a pose of the portion of the user, an orientation of the portion of the user, or a surface detail associated with the portion of the user.

19. The method as recited in claim 17, further comprising outputting content based at least in part on the portion of the information.

20. The method as recited in claim 17, further comprising:

generating content based at least in part on the portion of the information; and outputting the content.

* * * * *